(12) United States Patent
Lee

(10) Patent No.: US 7,264,610 B2
(45) Date of Patent: Sep. 4, 2007

(54) VOLUME-REGULATING DEVICE FOR MEDICAL FLUIDS

(75) Inventor: Jong Woo Lee, Seoul (KR)

(73) Assignee: Acemedical Co., Ltd., Koyang (KR)

( * ) Notice: Subject to any disclaimer, the term of this patent is extended or adjusted under 35 U.S.C. 154(b) by 143 days.

(21) Appl. No.: 10/822,593

(22) Filed: Apr. 12, 2004

(65) Prior Publication Data
US 2005/0075607 A1    Apr. 7, 2005

(30) Foreign Application Priority Data
Oct. 6, 2003    (KR) ...................... 10-2003-0069377

(51) Int. Cl.
*A61M 37/00* (2006.01)
(52) U.S. Cl. .................................... 604/131
(58) Field of Classification Search ............ 604/36–38, 604/65, 131–134, 136, 138, 151, 113, 156
See application file for complete search history.

(56) References Cited

U.S. PATENT DOCUMENTS

| | | |
|---|---|---|
| 3,980,083 A | 9/1976 | Elliott |
| 4,318,400 A | 3/1982 | Peery et al. |
| 4,411,652 A | 10/1983 | Kramer et al. |
| 4,741,733 A | 5/1988 | Winchell et al. |
| 4,904,239 A | 2/1990 | Winchell et al. |
| D324,911 S | 3/1992 | Sancoff et al. |
| 5,176,360 A | 1/1993 | Winchell et al. |
| 5,830,186 A | 11/1998 | Gonzales et al. |
| 5,846,216 A | 12/1998 | Gonzales |
| 6,024,724 A | 2/2000 | Lee |
| 6,312,411 B1 * | 11/2001 | Kanai .......................... 604/153 |

\* cited by examiner

*Primary Examiner*—Nicholas D. Lucchesi
*Assistant Examiner*—Christopher D Koharski
(74) *Attorney, Agent, or Firm*—Jordan and Hamburg LLP

(57) ABSTRACT

A volume-regulating device for medical fluids has a button body, which expands by an elastic protrusion, to overcome the problems arising from a conventional structure in which the elasticity is provided by coil springs. The present apparatus provides for the storage and the discharging of medical fluids, and by being formed into a single channel, not only enables manufacturing in a small size, but also achieves precise discharging of a volume of medical fluids.

4 Claims, 5 Drawing Sheets

VOLUME-REGULATING DEVICE FOR MEDICAL FLUIDS

Priority is claimed under the provisions of 35 USC § 119 based on Korean Patent Application No. 10-2003-0063977, filed Oct. 6, 2003.

BACKGROUND OF THE INVENTION

1. Field of the Invention

The present invention relates to a volume-regulating device for medical fluids that enables direct delivery by a patient of an additional volume of medical fluid discharged from a medical fluid supply apparatus, according to the level of pain experienced by the patient. Particularly, the present invention is characterized by preciseness in delivering the additional volume of medical fluid and by the inducement of accurate operation by use of a button body.

2. Technical Background and Description of the Prior Art

Currently, a volume-regulating device for medical fluids is the subject of Korean Laid-Open Patent Publication No. 2001-01031116, wherein a storage tube for medical fluid is provided inside, so that when additional delivery is needed, applying pressure on a button body causes medical fluid to be discharged from the storage tube for medical fluids and, thereby allows additional delivery. However, a disadvantage is that the operation of the button body is elastically actuated by multiple springs, therefore, unless pressure is applied on an exact location of the bottom body, precise operation is not achieved. Another disadvantage is that when pressure is applied to the storage tube for medical fluid in order to discharge medical fluid, medical fluid is dispersed to the directions of intake and exit, thus making it difficult to discharge a precise volume of medical fluids.

A conventional volume-regulator for medical fluids proposed for such use is subjected to Korea Laid-Open Patent Publication No. 2001-0103116, wherein, as shown in FIGS. 4 and 5, inside the cases (100, 100a) combining in counterparts with each other, is formed a medical fluid storage tube (300) to temporarily store a portion of the medical fluid, through a branch-conduit (200), which is discharged from a medical fluid supply apparatus thereof; are formed an intake (301) for storage and an exit (302) to discharge stored medical fluid on the above medical fluid storage tube (300) thereof; and is formed a check valve (304) on the above exit; at the intake (301) and at the medical fluid hose (303) is a supply tube (305) for delivery of a definite volume of medical fluid.

Furthermore, a button body for the purpose of applying pressure on the above medical fluid storage tube (300) is located on the upper part of the partition wall (500) formed to hold an internal space which can accommodate a medical fluid storage tube (300) therein; in order for the above button body (400) to operate in repetition, coil springs (600) are mounted to the inner recess groove (501) which is formed maintaining constant intervals on the inside of the partition wall (500); and in order to apply pressure to the above coil spring (600), pressurization protrusion (401) is radially formed on the button body (400); in order to prevent the above button body (400) from separating from the case (100) in a combined state by being elastically supported by coil springs (600), the opening (101) of the cover case (100a) is formed smaller than the circumference of the button body (400), thereby preventing the button body from separating from the case (100,100a).

Therefore, since the pressurization protrusion (401) is in a closely adhered state to the inner recess groove (501) of the partition wall (500), when and if sloping of the button body occurs, it becomes non-operational due to the angle of the sloping, or is unable to recover to its original state from an operating state, which is disadvantageous; in a situation when medical fluid is discharged after being stored, having the intake (301) and the exit (302) in separate locations causes discharging also to the direction of the intake (301), thus, the discharging of precise volume is not accomplished, which is disadvantageous.

SUMMARY OF THE INVENTION

Accordingly, in the present invention the intake and the exit are formed as one channel and a button body is formed as an elastic body, so that it operates elastically, thereby, inducing a precise operation of the button body despite pressure being applied to an inexact location.

The present invention solves the foregoing problems of the prior art by providing a button body which operates elastically by elastic force, in order to accomplish a precise application of pressure even when pressure is applied inexactly on the button body; and in addition, by forming the intake and the exit into one channel in order to achieve precise discharging.

For this purpose, the button body is elasticized, and on its outer side are formed expandable elastic protrusions of identical length; on the above elastic protrusions are formed fitting holes in order to fit and be fixed to a combining protrusion post that joins in counterpart with the case, which induces precise operation at all times. Moreover, configuring the intake and the exit into one channel on the medical fluid storage tube that is pressurized by the button body enables storage and discharging of a precise volume of the medical fluid.

DESCRIPTION OF THE PREFERRED EMBODIMENTS

The following is a detailed description of the most preferred embodiment of the present invention, referring to the attached drawings.

Figure 1:
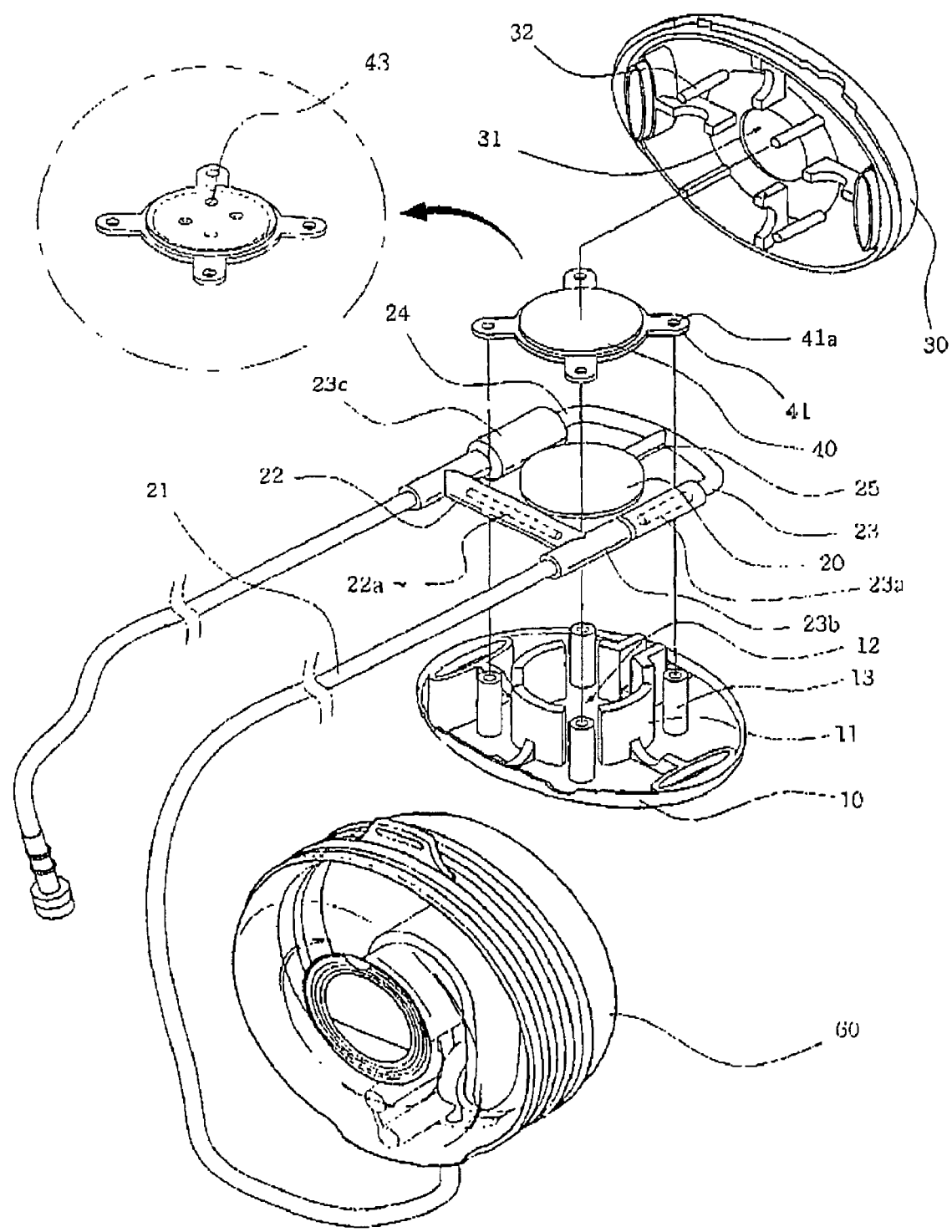
FIG. 1 is a perspective view of the present invention showing its constitution in accordance with its use.
Figure 2:
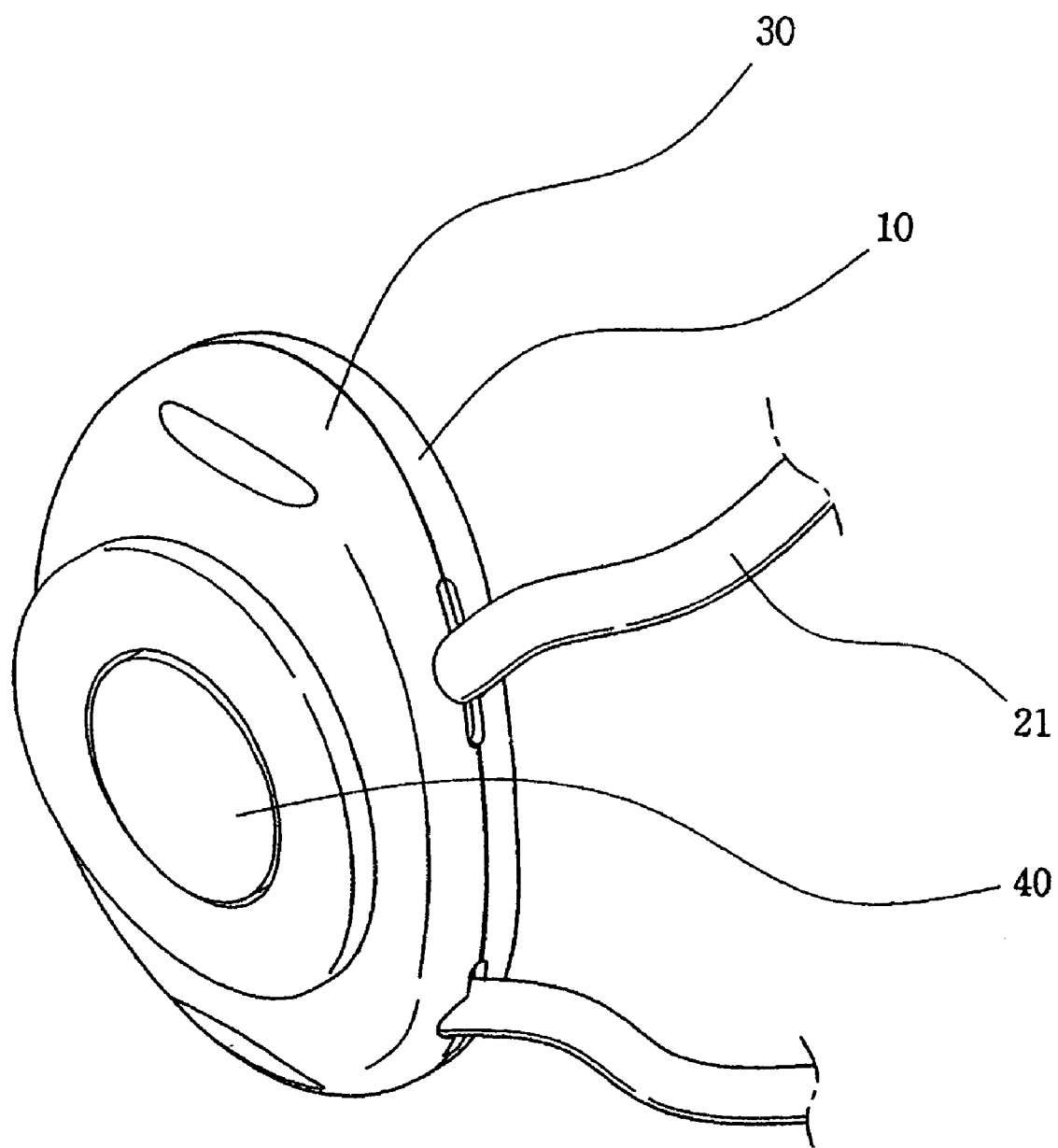
FIG. 2 is a perspective view of the outer appearance of the present invention.
Figure 3:
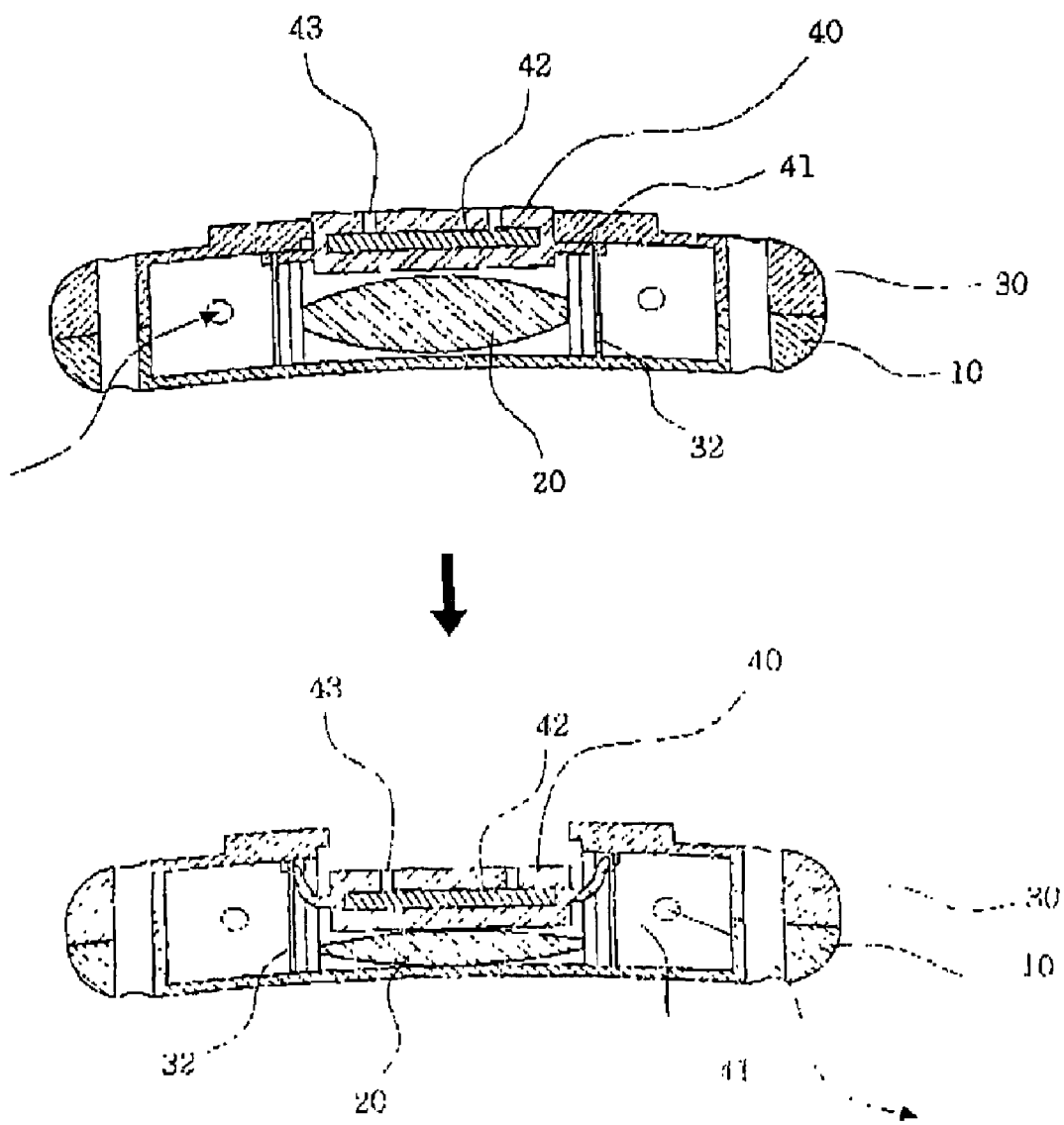
FIG. 3 is a cross-sectional view of the present invention in an operating state.
Figure 4:
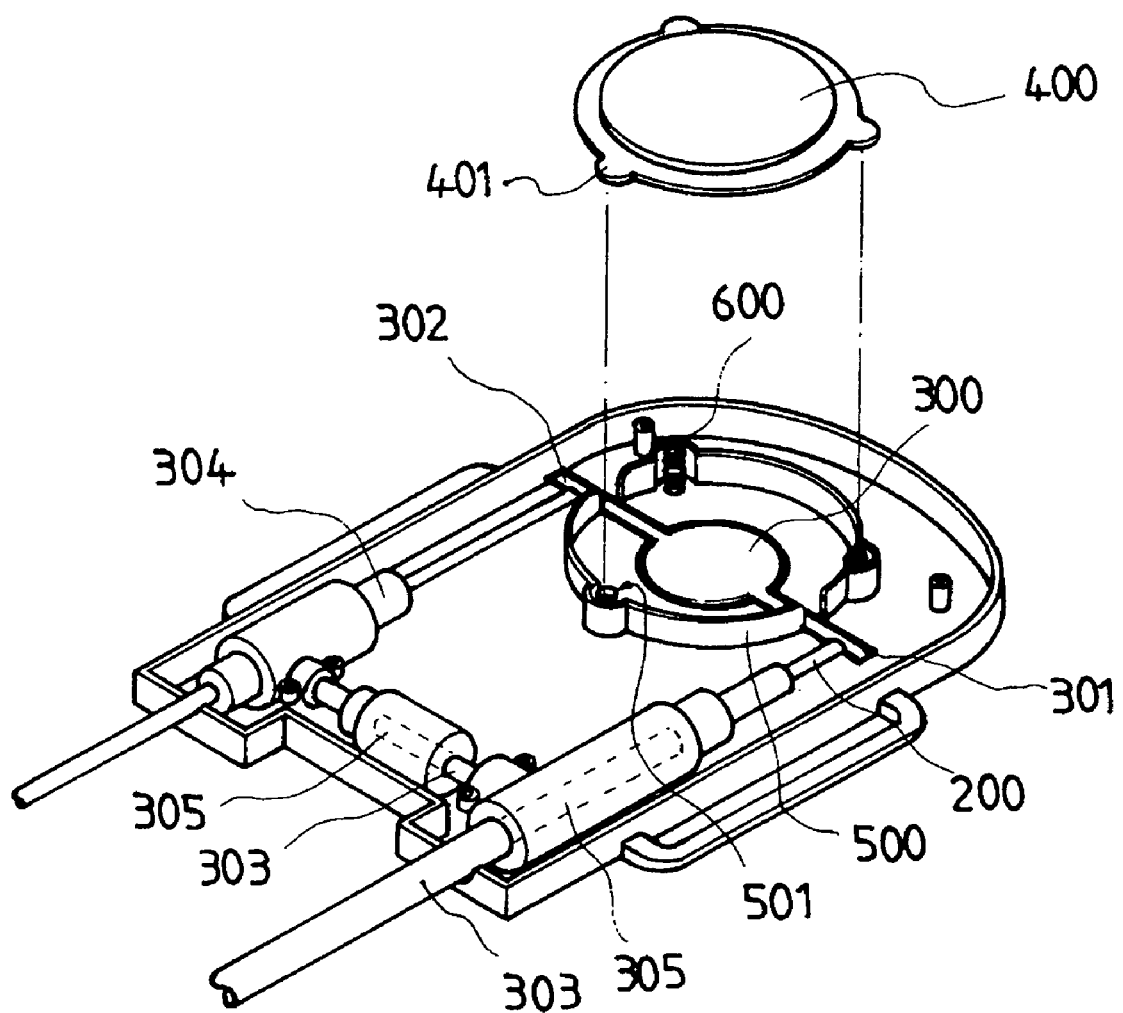
FIGS. 4 and 5 are perspective views showing the structure of a conventional volume-regulating device for medical fluid.
Figure 5:
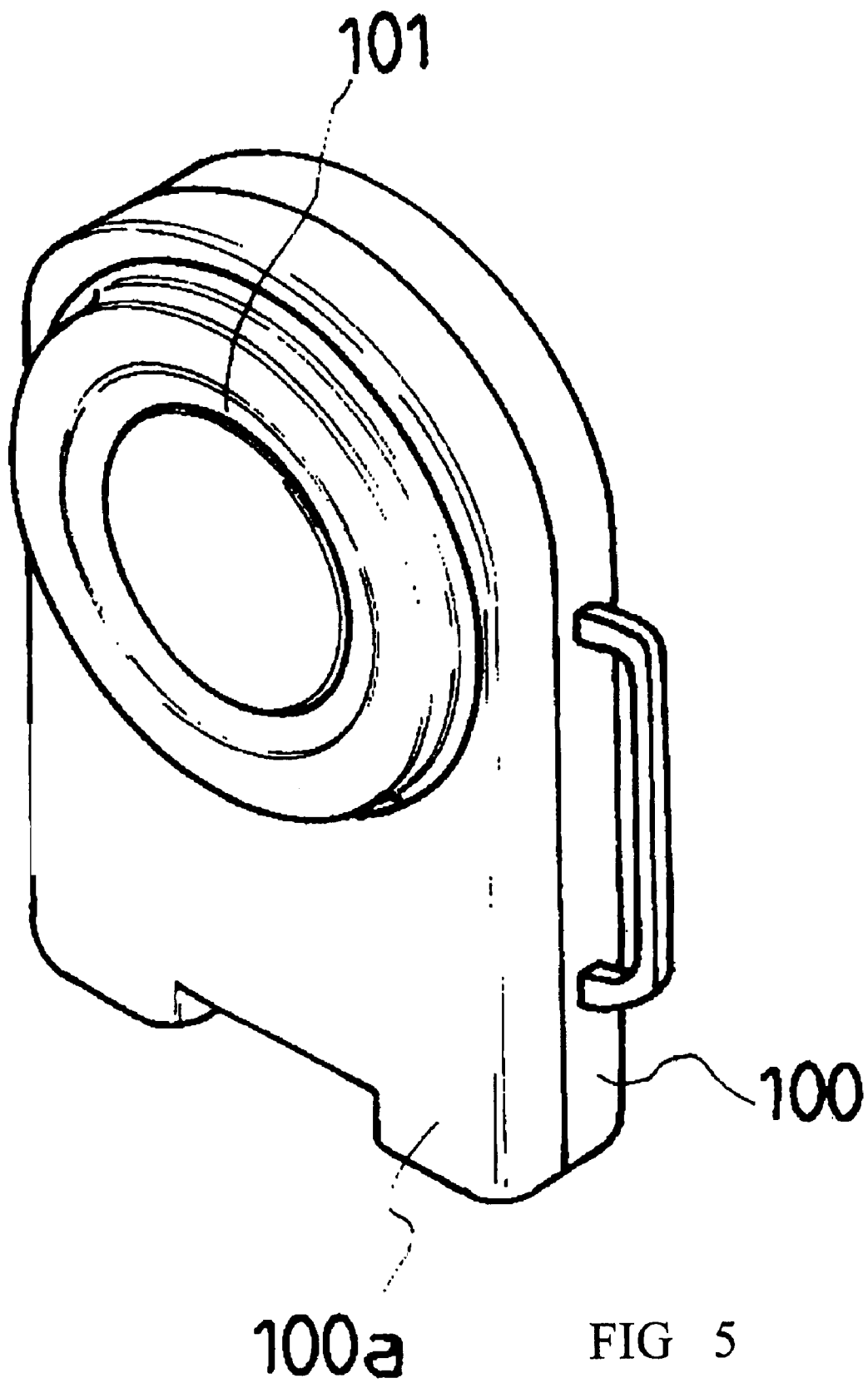

As shown in FIG. 1, a lower case (10) and an upper case (30) are joined by combining protrusion post (32) and combining protrusion tube (13); in the upper case (10) a medical fluid storage tube (20) is accommodated in the inside space which is provided by the divisional wall (11); the above medical fluid storage tube (20) is located below the through hole (31) in the upper case (30); the above through hole (31) is blocked by the button body (40), which has radial elastic protrusions (41), so that the button body (40) is exposed through the through hole (31); on each elastic protrusion (41) is formed a combining hole (41a) so that, when the lower case (10) and the upper case (30) are combined, it fits into the protrusion combining post (32) of the upper case (30) and joins with the combining protrusion tube (13), thereby, fixing the button body (40) in precise position of the through hole (31).

Then, for the combining hole (41a) of the elastic protrusion (41), a spline (not shown) can be used in order to prevent damage when operating elastically in a combined state with the combining protrusion post (32).

Furthermore, since the above button body (40) is formed as one body with the elastic protrusions (41), a reinforcing plate (42) is formed inside the button body (40) in order to complement suppleness of the button body (40), so that when pressure is applied to the button body (40), precise application of pressure to the medical fluid storage tube (20) can be achieved.

In this situation, the reinforcing plate can be formed by an insertion shaping method so that the entire reinforcing plate as one body is enclosed by an elastic body; and on the elastic body, formed by such shaping method, enclosing the reinforcing plate in order to locate the reinforcing plate (42) exactly in the center of the elastic body, holes (43) are formed through which posts (not shown) prepared on the mold are inserted.

This type of shaping method is known in the prior art, and is not further described herein.

Meanwhile, in the above medical fluid storage tube (20), medical fluid which discharges from the medical fluid supply apparatus (60) enters through the medical fluid inflow hose (21) and gets divided at the branch channel (23b) into the main supply channel (22) and the medical storage supply channel (23) and gets stored in the medical fluid storage tube (20).

Then, glass tubes (22a, 23a) are inserted both into the medical fluid main supply channel and the medical storage-supply channel (23), so that a constant volume can flow per constant interval of time.

Afterward, if pressure is applied to the button body (40) in order to discharge additional medical fluid, the medical fluid stored in the medical storage tube (20) is discharged into the medical fluid outflow channel (24) through a channel (25).

In a situation when the button body (40) puts pressure on the medical storage tube (20), the medial fluid filled in the medical fluid storage tube, wherein a glass tube (23a) with a minuscule diameter, formed on the medical fluid storage supply channel (23), preventing its reverse flow, is discharged only through the medical outflow channel (24).

In addition, employing a separate means for preventing reverse flow (23c) at the medical fluid outflow channel (24), results in preventing the medical fluid that entered through the medical fluid main supply channel (22) from flowing into the medical fluid storage tube (20).

Then, by forming only one channel (25) at the medical fluid storage tube (20), the phenomenon of discharging to the direction of the intake when discharging in the conventional method is eliminated, thus resulting in discharging of a precise volume.

Therefore, in the above volume-regulating device for medical fluids, if the combining protrusion post (32) of the upper case (30), when in a fitted state with the elastic protrusion (41) of the button body (40), is occluded and is combined with the combining the protrusion tube (13) of the lower case (10), the fixation of the button body (40) is completed and then, the button body (40) is exposed through the through holes (31) of the upper case (30), which are located in the precise position inside the case in a state being elastically supported.

Therefore, in the volume-regulating device of medical fluids with such structure, the button body (40) is formed as one body with the elastic protrusion (41), so that when any one side of the button body (40) is pressed due to the expansion of the elastic protrusion (41), it does not cause the button body to occlude with any one side of the divisional wall (11) of the lower case (10), thus, operating accurately upward and downward.

Furthermore, by forming an additional reinforcing plate (42) on the button body (40), so that in a situation when any one part of the button body (40) is pressed, pressure is applied integrally to the button body (40), and thereby preventing the phenomenon in which the button body (40) gets pressed sloping to one side; thereby performing a smooth operation of the button body (40).

| | |
|---|---|
| 10. Lower case | 11. Divisional wall |
| 12. Inside space | 13. Combining protrusion tube |
| 20. Storage tube for medical fluid | 30. Upper case |
| 31. Through hole | 32. Combining protrusion post |
| 40. Button body | 41. Elastic protrusion |
| 42. Reinforcing plate | 43. Holes |

The invention claimed is:

1. A volume-regulating device for medical fluids, comprising:
   an upper case and a lower case which engagingly cooperate with one another;
   a medical fluid storage tube disposed in an inner space of said lower case;
   a button body disposed above said fluid storage tube, for applying pressure to said medical fluid storage tube, said button body being accessible from an exterior of said device through a hole in said upper case;
   a plurality of elastic protrusions positioned radially on a periphery of said button body;
   a plurality of axially extending combining protrusion posts on said upper case; and
   a plurality of combining protrusion tubes located on said lower case;
   said combining protrusion posts each cooperate with ones of said combining protrusion tubes and ones of said elastic protrusions when said upper case and said lower case engagingly cooperate with one another, and whereby when said button body alternatively operates in a downward and an upward direction, pressure is uniformly applied to said storage tube and released therefrom.

2. The device according to claim 1, wherein said medical storage tube has an inlet and an outlet, which are formed as a single channel.

3. The device of claim 1, wherein said button body is an elastic body, with a radially extending reinforcing plate formed therein whereby pressure provided through said hole in said upper case is transmitted to a top surface of said medical fluid storage tube and dispersed evenly over said top surface of said medical fluid storage tube.

4. The device of claim 1 wherein said combining protrusion posts comprise four combining protrusion posts which are circumferentially spaced and are integral with said upper case.

* * * * *